(12) United States Patent
Perlinger et al.

(10) Patent No.: US 8,485,020 B2
(45) Date of Patent: Jul. 16, 2013

(54) SEMIVOLATILE ORGANIC CHEMICAL SAMPLING AND EXTRACTION TRANSFER METHOD AND APPARATI

(76) Inventors: Judith Ann Perlinger, Chassell, MI (US); Mark David Rowe, Houghton, MI (US)

( * ) Notice: Subject to any disclaimer, the term of this patent is extended or adjusted under 35 U.S.C. 154(b) by 1177 days.

(21) Appl. No.: 12/324,271

(22) Filed: Nov. 26, 2008

(65) Prior Publication Data
US 2012/0090411 A1 Apr. 19, 2012

Related U.S. Application Data

(60) Provisional application No. 60/990,333, filed on Nov. 27, 2007.

(51) Int. Cl.
*G01N 30/04* (2006.01)
*G01N 1/28* (2006.01)
*G01N 1/22* (2006.01)

(52) U.S. Cl.
USPC .............. 73/23.41; 73/863.12; 73/863.23

(58) Field of Classification Search
USPC .............. 73/23.41, 23.42, 863.12, 863.23
See application file for complete search history.

(56) References Cited

U.S. PATENT DOCUMENTS

| 5,763,360 | A | 6/1998 | Gundel et al. |
| 6,226,852 | B1 | 5/2001 | Gundel et al. |
| 6,780,818 | B2 | 8/2004 | Daisey et al. |

OTHER PUBLICATIONS

Perlinger, J.A. et al., "Evaluation of Novel Techniques for Measurement of Air—Water Exchange of Persistent Bioaccumulative Toxicants in Lake Superior", Environmental Science and Technology, vol. 39, No. 21, 2005, pp. 8411-8419.*
Great Lakes Air Deposition (GLAD) Program: Quarterly Progress Report: Jul. 1-Sep. 30, 2006, Submitted by Michigan Technological University, 2006, pp. 1-6.*
Mader, B.T. and Pankow, J.F. (2001) "Gas/Solid Partitioning of Semivolatile Organic Compounds (SOCs) to Air Filters. 3. An Analysis of Gas Adsorption Artifacts in Measurements of Atmospheric SOCs and Organic Carbon (OC) When Using Teflon Membrane Filters and Quartz Fiber Filters", Environ. Sci. Technol. 35, 3422-3432.
Krieger, M.S. and Hites, R.A. (1992) "Diffusion denuder for the collection of semivolatile organic compounds", Environ. Sci. Technol. 26, 1551-1555.
Mader, B.T., Flagan, R.C. and Seinfeld, J.H. (2001) "Sampling atmospheric carbonaceous aerosols using a particle trap impactor/denuder sampler" Environ. Sci. Technol., 35, 4857-4867.

(Continued)

*Primary Examiner* — Daniel Larkin
(74) *Attorney, Agent, or Firm* — Dunlap Codding, P.C.

(57) ABSTRACT

One way of practicing the method of the invention is to follow these steps, not necessarily in the disclosed sequence: (1) providing a hot gas spike apparatus to load one or more diffusion denuders with a compound selected from the group consisting of a calibration standard, an internal standard, and a surrogate standard compound in a solvent carrier; (2) pulling one or more samples of ambient atmosphere through at least one of the diffusion denuders in a multicapillary collection device; (3) extracting analytes from at least one of the diffusion denuders in an analyte transfer apparatus or from a filter using an extraction device; (4) optionally cleaning up gaseous extracts or extracts of filters using chromatography, and transferring the collected analytes into an analytical device. To practice the method, an apparatus is disclosed that has a hot gas spike component, a high-flow multicapillary collection device and an analyte transfer apparatus.

18 Claims, 5 Drawing Sheets

OTHER PUBLICATIONS

Gundel, L.A. and Lane, D.A. (1999) Sorbent-Coated Diffusion Denuders for Direct Measurement of Gas-partitioning by Semi-volatile Organic Compounds, In Gas and Particle Phase Measurements of Atmospheric Organic Compounds (Lane, D.A. Ed.) pp. 287-332, Gordon and Breach Science Publishers, Amsterdam, The Netherlands.

Ortner, E.K. and Rohwer, E.R., Trace Analysis of semi-volatile organic air pollutants using thick film silicone rubber traps with capillary gas chromatography, J. High Resol. Chromatogr., 19, 339-344, (1996).

Science Beat, Berkeley Lab "Air Sampler Zeros in on Atmospheric Pollutants", Sep. 1, 1999 (reporting the work of Laura Gundel).

Tobias, David, E., Perlinger, Judith A., et al., "Direct thermal desorption of semivolatile organic compounds from diffusion denuders and gas chromatographic analysis for trace concentration measurement" Journal of Chromatography A, 1140 (2007) 1-12.

Possanzini, M., Febo A., and Liberti, A., "New Design of A High-Performance Denuder for the Sampling of Atmospheric Pollutants", Atmospheric Environment vol. 17, No. 12, pp. 2605-2610 (1983).

Krieger, Mark S. and Hites, Ronald A., "Measurement of Polychlorinated Biphenyls and Polycyclic Aromatic Hydrocarbons in Air with a Diffusion Denuder", Environ. Sci. Technol. 1994, 28, 1129-1133.

Lewis, Robert G. and Coutant, Robert W., "Determination of Phase-Distributed Polycyclic Aromatic Hydrocarbons in Air by Grease-Coated Denuders", U.S. Environmental Protection Agency, North Carolina; Battelle, Columbus, Ohio, p. 201-231.

Eatough, Delbert J., "Boss, The Brigham Young University Organic Sampling System: Determination of Particulate Carbonaceous Material Using Diffusion Denuder Sampling Technology", Department of Chemistry and Biochemistry, Brigham Young University, Provo, UT, p. 233-285.

Coutant, Robert W., Callahan, Patrick J., Kuhlman, Michael R, and Lewis, Robert G., "Design and Performance of A High-Volume Compound Annular Denuder", Atmospheric Environment vol. 23 No. 10 pp. 2205-2211 (1989).

"Identification of Iris Scent Volatiles Using Dynamic Headspace with PDMS Foam Trapping and GC-TOFMS"; Ray Marsili and Cesar Kenaan, Marsili Consulting Group; Perfumer & Flavorist, vol. 32 Nov. 2007, p. 18-32.

Extended European Search Report, Application No. EP 09 17 6403, dated Oct. 21, 2010.

Rowe, Mark and Perlinger, Judith A.; Thermal Extraction and Analysis of Atmospheric Semivolatile Organic Compounds From Multicapillary Collection Devices; Organohalogen Compounds, vol. 70 (2008) pp. 0038-0041.

* cited by examiner

US 8,485,020 B2

SEMIVOLATILE ORGANIC CHEMICAL SAMPLING AND EXTRACTION TRANSFER METHOD AND APPARATI

CROSS-REFERENCE TO RELATED APPLICATION

This non-provisional application claims the benefit under 35 U.S.C. §119(e) of U.S. provisional application Ser. No. 60/990,333 that was filed on 27 Nov. 2007.

BACKGROUND OF THE INVENTION

1. Field of the Invention

The disclosed method and apparatus relate to systems for studying air quality. More specifically, the invention relates to low-volume, high-volume and passive atmospheric sampling for the determination of semivolatile organic chemical (SOC) concentration.

2. Background Art

Semivolatile organic compounds (SOCs) are typified by low volatility, exhibiting vapor pressures from $10^1$ to $10^{-6}$ Pa and consequently low vapor-phase concentrations in ambient air (concentrations of ca. pg m$^{-3}$; mixing ratios of ca parts-per-quadrillion by volume (ppqv)). Synthetic SOCs are used in a wide range of products such as pesticides, flame retardants, plasticizers, and lubricants. Many SOC's are also classified as persistent bioaccumulative toxicants (PBTs) because of their long environmental lifetimes (persistence), their tendency to accumulate in the tissue of animals (bioaccumulate), and adverse health effects to humans or other organisms (toxic). Anthropogenic and synthetic SOCs also influence climate through reactions with organic particles.

As awareness of the toxic effects and relevance to climate of SOCs has grown, so has the need to understand their transport and fate in ambient air. In addition, because vapor-phase and particle-bound SOCs may have significantly different transport mechanisms, health impacts, and influences on climate, accurate separation and collection of vapor-phase and particle-phase SOCs is desirable.

SOC sampling techniques include active and passive methods. The two most common methods are 'high volume', an active method, which samples large quantities of ambient air e.g., from 400 to 4000 m$^3$ in order to collect sufficient quantities of analytes, and various passive methods that rely on diffusion of SOCs into the trapping medium to gather analytes in the absence of advection. These techniques typically employ solvent extraction to liberate the collected analytes from the sampling media, which results in sample dilution and an increase in both the required sample volume and time required to gather that volume. Separation of vapor and particulate phases is not possible with passive samplers, which collect primarily gas-phase compounds. High-volume samplers, when employed in their typical configuration with a particulate filter anterior to the vapor phase sorbent, suffer from sampling artifacts that may confound the differentiation between gas- and particle-phase SOCs.

Conventional High-Volume Sample Collection and Analysis by Soxhlet Extraction, Column Chromatography, and Concentration.

This sampling and analysis technique has been in use for ca. 30 years to measure ambient air concentrations of semivolatile organic compounds, and is considered to be the "workhorse" of SOC monitoring programs world-wide. It involves collection of particle-phase compounds on filters followed by collection of gas-phase compounds in XAD resin or polyurethane foam (PUF) plugs at a flow rate of from 40-1000 L min$^{-1}$ (typically 700 L min$^{-1}$). The resin or PUF plugs and filters are subsequently processed using Soxhlet extraction, column chromatography to clean up the extract, and concentration of the solvent extract by roto-evaporation and/or solvent blow-down. The mass of analyte in the extract is then analyzed by injecting a small volume of the extract (ca. $\frac{1}{100}$$^{th}$ of the solvent volume) into a gas chromatograph.

There are certain problems with prior approaches:

1. It is known that gaseous and particle-phase chemicals are incompletely separated using high-volume air sampling. Research directed at quantifying and correcting for the artifacts has been conducted. The particle-phase compounds can be desorbed during the long sampling times required (hours to days), in part due to diurnal temperature changes during sampling, while some gas-phase compounds can sorb to the filter.
2. There is a significantly increased opportunity for losses to occur during the analytical procedures to extract and analyze the compounds as compared to, for example, thermal extraction into minitubes and subsequently into the gas chromatograph.
3. Because only a small portion of the analytes collected are actually injected into the gas chromatograph, the sampling time must be correspondingly longer to collect adequate sample mass at the comparable flow rates that are employed (40-1000 L min$^{-1}$). Analyte concentrations and meteorological conditions can change over the sample collection time, with consequent losses in resolution of analyte concentrations in a sample as well as introduction of potential artifacts due to changing sorbent properties within the sampler under varying meteorological conditions.
4. Many of the prior art sample processing steps are relatively expensive and they entail an increased sample turn-around time.
5. High-volume sampling and analysis require significant amounts of solvent and XAD resin, neither of which can be re-used (unless PUF is used as a sorbent rather than XAD), and thus these techniques are less sustainable.

Passive Sampling and Analysis of Combined (Gas and Particulate) Semivolatile Organic Chemicals by Soxhlet Extraction, Column Chromatography, and Concentration.

Passive sampling has been utilized to collect SOCs in ambient air. This technique is similar to high-volume air sampling except that compounds are collected in PUF by passive diffusion in an estimated volume of air sampled over a time period of weeks to months, rather than by actively drawing air through XAD resin or PUF. The required sample processing steps are the same as for analysis of XAD resin or PUF as described above. A recently developed version of a passive sampler, a "flow-through" sampler allows considerable shortening of the required sampling time, but the other issues with passive sampling still exist using this version.

Although passive sampling produces a concentration averaged over the entire sampling period, that period is on the order of weeks to months. No information can be gathered on short term variations in concentration of collected compound concentrations. In addition, variations in meteorological conditions during lengthy passive sampling periods can lead to variations in amount of SOC collected, making spatial comparisons of estimated concentrations inappropriate over large regions where local meteorology differs. Thus, application of passive sampling technology must be limited to cases in which its constraints are acceptable.

Certain disadvantages of passive sampling and analysis include increased opportunity for losses to occur during the analytical procedures to extract and analyze the compounds as compared, for example, to thermal extraction into minitubes and subsequently into the gas chromatograph, higher expense of analysis, greater time required for analysis, consequent increased sample turn-around time, and decreased sustainability of solvent usage.

Diffusion Denuders.

A "denuder" is a device that traps gas and allows particles to be collected separately. Diffusion denuders have been developed in various shapes and sizes for analysis of charged and neutral chemicals including annular, parallel plate, capillary, and honeycomb structures. Some diffusion denuders can be coated with various sorbents including silicone grease, crushed Tenax-GC™ and Florisil, silicone gum, and crushed Tenax-GC™ applied onto silicone gum. In addition, various analyte extraction techniques have been attempted including solvent extraction, supercritical fluid extraction, and thermal desorption, but solvent extraction is typically employed.

It is known to use sticky resin beads whose pores are sized so as to trap molecules of organic gases—small enough to adhere through friction alone to a sand-blasted inner surface of a glass tube. *Science Beat, Berkeley Lab "Air Sampler Zeros In On Atmospheric Pollutants"*, Sep. 1, 1999 (*reporting the work of Lara Gundel*). In operation, solid particles are relatively massive and travel straight through a denuder. Gas molecules, however, eventually hit a wall and stick. Depending on air flow and the length of tube, particles may stay airborne, but long enough for gas to become trapped. Id.

In one approach, after an air sample is sucked through the denuder, the particle filter is removed and gas trapped on the resin beads is extracted and analyzed. Capillary diffusion denuders are known that use sections of commercial gas chromatography, fused silica capillary columns bundled together and encapsulated with expoxy. However, cracking of the epoxy during repeated thermal cycling has recurred.

Annular Denuder System.

The prior art includes diffusion denuders made from annular sandblasted glass channels coated on the inside with ground XAD-4 resin. See, e.g., U.S. Pat. Nos. 6,226,852 and 6,780,818. The systems are presently marketed containing uncoated annular denuders by URG Corporation (Chapel Hill, N.C.; http://www.urgcorp.com), but denuders coated to specification alone were previously marketed by Restek, Inc. These annular diffusion denuders must be re-coated after being used 20 times for sample collection and solvent extraction of analytes.

Several technical challenges are therefore presented by prior approaches:

1. Design of a durable sampling device utilizing diffusion denuders for separation of gaseous SOCs and particle-associated SOCs that can be manufactured inexpensively from commercially available materials. Ideally, the SOC sampling device should have the capability to enable analytes to be extracted thermally into an analytical device to measure the gaseous SOCs and particle-associated SOCs at concentrations found in ambient air.
2. Design of a system to transfer and concentrate analytes by thermal extraction (analyte transfer apparatus). It would be desirable to have a system that accommodates the need for a high flow rate to extract analytes from the larger diameter denuder (several hundreds of liters per minute), while achieving quantitative and complete transfer of analytes into the analytical column in the gas chromatograph, which can only accept flows of ca 2 mL min$^{-1}$.
3. Design of a hot gas spike apparatus to uniformly distribute surrogates and standards in denuders in the gas phase.
4. Development of custom-packed minitubes and gas chromatograph inlet liners. Ideally, such minitubes and liners should be capable of trapping more-volatile SOCs (e.g., hexachlorocyclohexane) while having low reactivity and the capability to quantitatively release reactive, low-volatility SOCs at high temperatures (300° C.).

Thus, conventional high-volume and passive atmospheric sampling (indoors and outdoors) for determination of semivolatile organic chemical (SOC) concentration in gas and particle-associated phases require long sampling periods because only a small portion of the analytes collected are typically analyzed in a gas chromatograph, or in the case of passive and flow-through sampling, no phase separation.

SUMMARY OF THE INVENTION

The invention has method and apparatus aspects.

One way of practicing the method of the invention is to follow these steps, not necessarily in the disclosed sequence:

1. providing a hot gas spike apparatus to load one or more diffusion denuders with a compound selected from the group consisting of a calibration standard, an internal standard, and a surrogate standard compound in a solvent carrier;
2. pulling one or more samples of an ambient atmosphere through at least one of the diffusion denuders in a multicapillary collection device;
3. extracting analytes from at least one of the diffusion denuders in an analyte transfer apparatus using a desorption device,
4. optionally cleaning up gaseous extracts or extracts from a filter using chromatography; and
5. transferring the collected analytes into an analytical device.

To practice the method, an apparatus is disclosed that has a hot gas spike component, a multicapillary collection device and an analyte transfer apparatus. In one embodiment this apparatus separates and collects gaseous and particle-associated SOCs present in trace amounts in an indoor or outdoor atmosphere under ambient temperature, pressure, and humidity conditions.

One objective of the invention is to achieve similar or better detection limits to conventional methods of SOC collection and analysis while offering the advantages of diffusion denuder sampling and analysis.

A sampling and extraction system has been developed that offers significantly faster sampling times with more efficient and inexpensive methods for studying air quality.

The system provides a method of separating SOCs in gas and particulate phases using the multicapillary collection device and of subsequently transferring them into receptacles such as minitubes that are extracted into a chromatograph for analysis.

The transfer process also provides an opportunity for gas-phase sample cleanup. For example, polar organics present in the air may interfere with non-polar target analytes without an additional cleanup step. The interfering polar organic compounds can be removed from the gas stream prior to capture of SOCs.

DETAILED DESCRIPTION OF THE PREFERRED EMBODIMENT(S)

Figure 5:
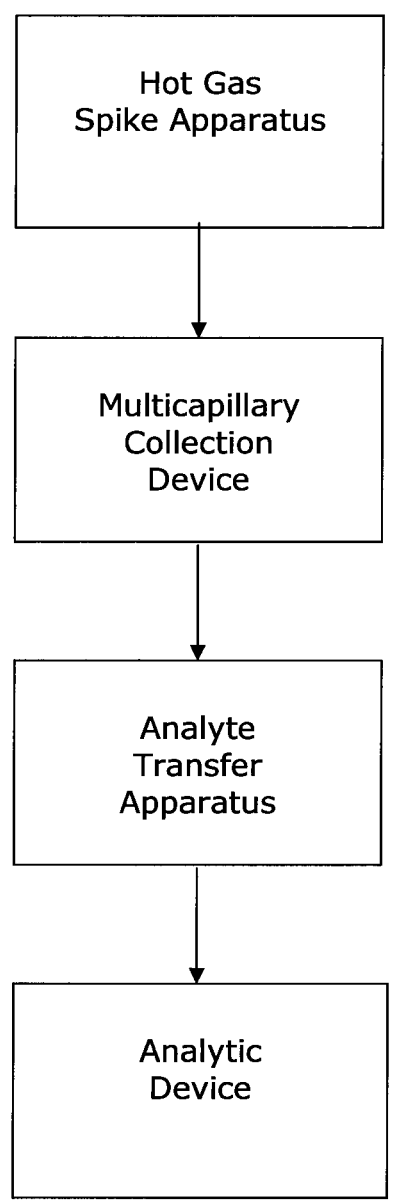
FIG. 5 is a schematic view of an exemplary embodiment of a semivolatile organic chemical collection and extraction system.

One embodiment of the apparatus of the invention, schematically shown in FIG. 5, includes three components that are designed to separate and collect gaseous (concentrations in the gas-phase as low as $pg/m^3$ or as low as mixing ratios of parts-per-quadrillion by volume) and particle-associated semivolatile organic chemicals (SOCs) present in trace amounts in an indoor or outdoor atmosphere under ambient temperature, pressure, and humidity conditions and subsequently transfer them into, for example, minitubes that are extracted into an analytic device for analysis.

The three components are:
(1) a multicapillary collection device (MCCD);
(2) a hot spike gas apparatus (HSGA); and,
(3) an analyte transfer apparatus (ATA).

1. The Multicapillary Collection Device (MCCD)

Figure 1:
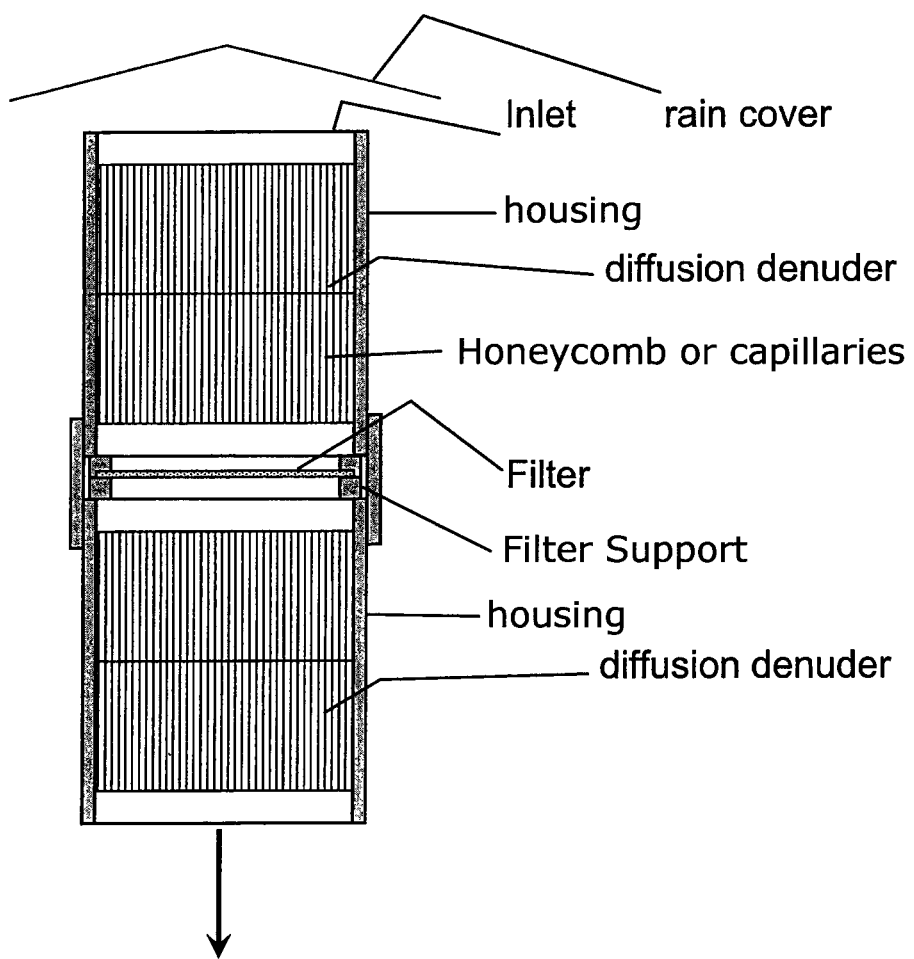
FIG. 1 depicts one embodiment of a multicapillary collection device.

Semivolatile organic chemicals in gas and particulate phases are separated and collected from ambient (indoor or outdoor) air in the MCCD (FIG. 1). Known masses of target analytes, internal standards, and/or surrogate standards are injected into MCCDs using a hot gas spike apparatus (discussed below). Analytes are transferred from MCCDs into receptacles, such as minitubes using the ATA (also discussed below).

The MCCD separates and collects gaseous and particle-associated SOCs by drawing air through it at a high flow rate in one embodiment (nominal value 300 L $min^{-1}$). MCCDs separate gaseous and particle-associated SOCs in air due to the difference in diffusivities of these phases under laminar flow conditions in capillaries. Smaller gases diffuse to the walls in the capillaries before exiting the diffusion denuder. Particles and associated chemicals exit diffusion denuders where they are trapped on a filter (e.g. Whatman Glass Fiber Filter—GFF). In one approach, semivolatile organic chemicals that are desorbed from particles or the filter itself during sampling are trapped on one or more backup diffusion denuders.

The MCCD is modular. One embodiment includes an aluminum housing containing, in series, two 2-in long, 4 in-OD, 1/32" cell size honeycomb (or capillary) diffusion denuders, a 4-in-OD filter and filter support, and two 2-in long, 4-in OD, 1/32" cell size backup honeycomb (or capillary) diffusion denuders. As an example, the vacuum required to pull 300 L/min through this device is 73 mm Hg, relative to atmospheric pressure, and 1.1 mm Hg relative to atmospheric pressure without the filter. In one embodiment, the multicapillary collection device permits a flow rate of approximately 600 L/min.

Low head loss in this sample collection system is an advantage over conventional systems that employ granular sorbent beds or foam plugs as sorbents.

If present, the honeycomb optionally is made of stainless steel. It may be given a deactivation treatment (such as Restek Inc.'s Sulfinert treatment) after being inserted into a stainless steel sleeve. It is anticipated that ceramic honeycomb materials could be advantageously substituted for stainless steel. In another embodiment, the multicapillary collection device comprises capillaries fabricated from fused silica.

Following deactivation, the honeycombs in their sleeves optionally are coated with a stationary phase (e.g., Rtx-1, a crosslinked polydimethylsiloxane, prepared by Restek).

In certain applications the stainless steel honeycomb could be eliminated and replaced with commercially available tubing composed of a primary component of the Rtx-1 stationary phase. The use of a small version of this type of denuder, to collect and analyze small organic compounds was reported by Ortner and Rohwer (Ortner, E. K., and Rohwer, E. R. (1996), "Trace Analysis of Semi-volatile Organic Air Pollutants Using Thick Film Silicone Rubber Traps with Capillary Gas Chromatography," *J. High Resol. Chromatog.* 19, 339-344, which is incorporated herein by reference).

This apparatus may include one or more diffusion denuders with a low-flow (13 L $min^{-1}$) rate in which a polyimide resin can be used as the encapsulating medium inside a deactivated stainless steel tube. The polyimide resin has comparable thermal stability as gas chromatography columns with which the resin is used to coat the columns (to decrease brittleness) in commercial applications (better than epoxy), and provides repeated sampling and thermal extraction of collected SOCs from the low-flow diffusion denuders with no cracking.

The stationary phase with which the capillary column sections are coated on the inside in the low-flow diffusion denuder resembles that used to coat the high-flow diffusion denuders in MCCDs (Rtx-1).

The analysis procedure for low-flow diffusion denuders utilizes thermal extraction of collected analytes from the diffusion denuders into a cryogenically-cooled PTV inlet of a gas chromatograph or into minitubes for sample cleanup.

Because of the lower dead-volume in low-flow diffusion denuders as compared to MCCDs, transfer of analytes using an ATA is unnecessary prior to extraction into the inlet of a chromatograph (e.g., a gas chromatograph). However, it is necessary to carry out this off-line analyte transfer step given the large dead-volume of the high-flow apparatus. But an inadequate mass of analytes can be collected in low-flow diffusion denuders under some ambient air conditions (e.g., outdoor rural or remote environments for polychlorinated biphenyls (PCBs)). With cleanup, adequate concentrations of PCBs to measure are obtained in indoor environments.

2. Hot Gas Spike Apparatus (HSGA)

Figure 2:
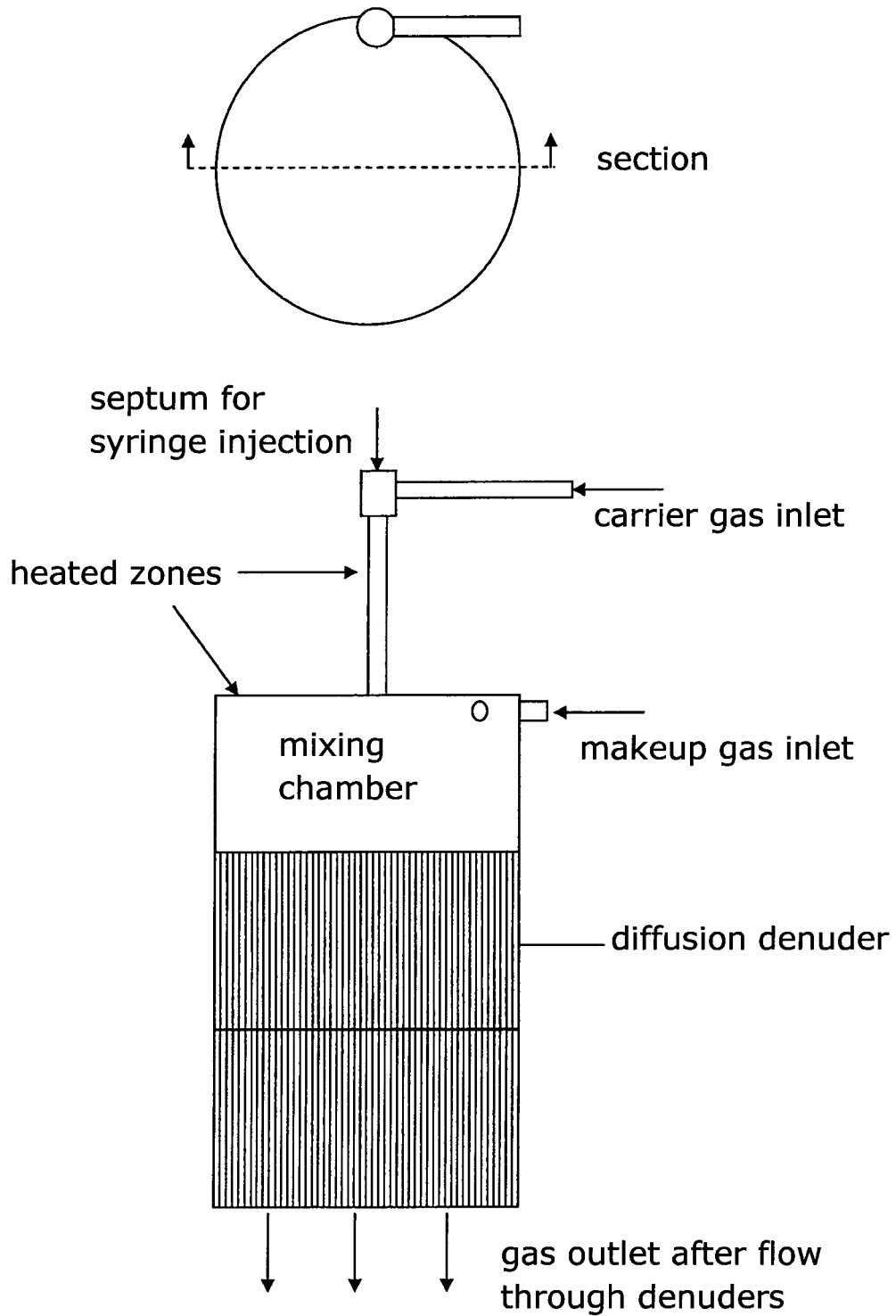
FIG. 2 depicts one embodiment of a hot gas spike apparatus.

In the hot gas spike apparatus (FIG. 2) a stream of carrier gas at ambient temperature is in one embodiment introduced in a direction preferably perpendicularly to the heated gas stream, and tangentially to the circular wall of the mixing chamber to provide a zone of turbulent mixing and uniform distribution of flow throughout the cross-section of the denuder diameter. The heated walls of the mixing chamber minimize or prevent condensation of analytes on the walls. Optional cooling of the gas stream prior to entering the denuder allows the denuder to remain near room temperature and trap analytes without the need for additional cooling of external surfaces of the denuder. If desired, heated zones are monitored using thermocouples and temperature controller.

Diffusion denuders can optionally be spiked by a syringe with known masses of target analytes, internal standards, and/or surrogate standards in a solvent using the hot gas spike apparatus. Surfaces downstream of the injection point and upstream of the denuder are optionally heated to a temperature sufficient to prevent condensation of analytes, typically 230 to 300° C. These surfaces are optionally deactivated (Sulfinert treatment, Restek) downstream of the injection point and upstream of the denuder in a mixing chamber where carrier gas at ambient temperature is mixed with the heated gas stream carrying analytes. The flow rate of the ambient temperature carrier gas is sufficiently high, about ten times the flow rate of heated gas, such that the gas stream is cooled by mixing to near ambient temperature prior to entering the denuder.

The technology in this disclosure has numerous advantages over prior annular diffusion denuders:

First, SOCs in diffusion denuders and filters in MCCDs can be extracted thermally or by using solvent extraction with sonication. Use of thermal extraction avoids having to carry out subsequent solvent-based cleanup and concentration steps required for high-volume sample extract and passive sample extract processing, with associated increased time and potential for analyte loss.

Second, analytes in MCCDs can be virtually completely transferred into an analytic device such as a gas chromatograph (GC). Only a fraction of the solvent extract from the annular diffusion denuder system is injected, limiting the mass of analyte that is injected into the analytic device.

Third, annular denuder handling abrades the optional XAD-4 that may coat the surface such that the surfaces must be re-coated, as mentioned earlier, after 20 uses. The low-flow diffusion denuders (containing commercial capillary column sections with the same stationary phase as the high-flow diffusion denuders in MCCDs) have shown no sign of limited life such as this in 5 years of usage. This reduces expenses and the time associated with repeated surface treatment.

Fourth, the flow rate achievable using MCCDs is higher than that of the annular diffusion denuder system (up to 200 L min$^{-1}$ for the jumbo Integrated Organic Gas and Particle Sampler—IOGAPS). A longer sampling time (with the potential for meteorological and ambient air concentration changes) is required for use of the annular diffusion denuder system if an identical analyte transfer process is used.

Fifth, headloss through the annular denuder system is higher when a backup XAD or PUF sorbent trap is used. The vacuum required to pull 300 L min$^{-1}$ of air through a MCCD containing a particle-free 4-in glass fiber filter is 73 mm Hg, relative to atmospheric pressure, and 1.1 mm Hg relative to atmospheric pressure without the filter. Headloss through the annular denuder system with a backup XAD or PUF sorbent trap will be significantly higher. Higher headloss means a higher driving force for desorption of analytes in the devices as well as higher power demands.

Sixth, retention time of air within the MCCD cells at a flow rate of 300 L min$^{-1}$ is 0.147 seconds. This value is lower by ca. 0.5-0.1 that of the Integrated Organic Gas and Particle Sampler (IOGAPS built for a tobacco-smoke study) device depending on flow rate through the device, and the same as or down to 0.2 that of the jumbo IOGAPS device depending on flow rate. The lower retention time decreases the time in which the equilibrium between gaseous and particulate phase semivolatile compounds can be disturbed. This lessens the time in which secondary organic aerosol formation may occur prior to phase separation.

3. The Analyte Transfer Apparatus (ATA)

Figure 3:
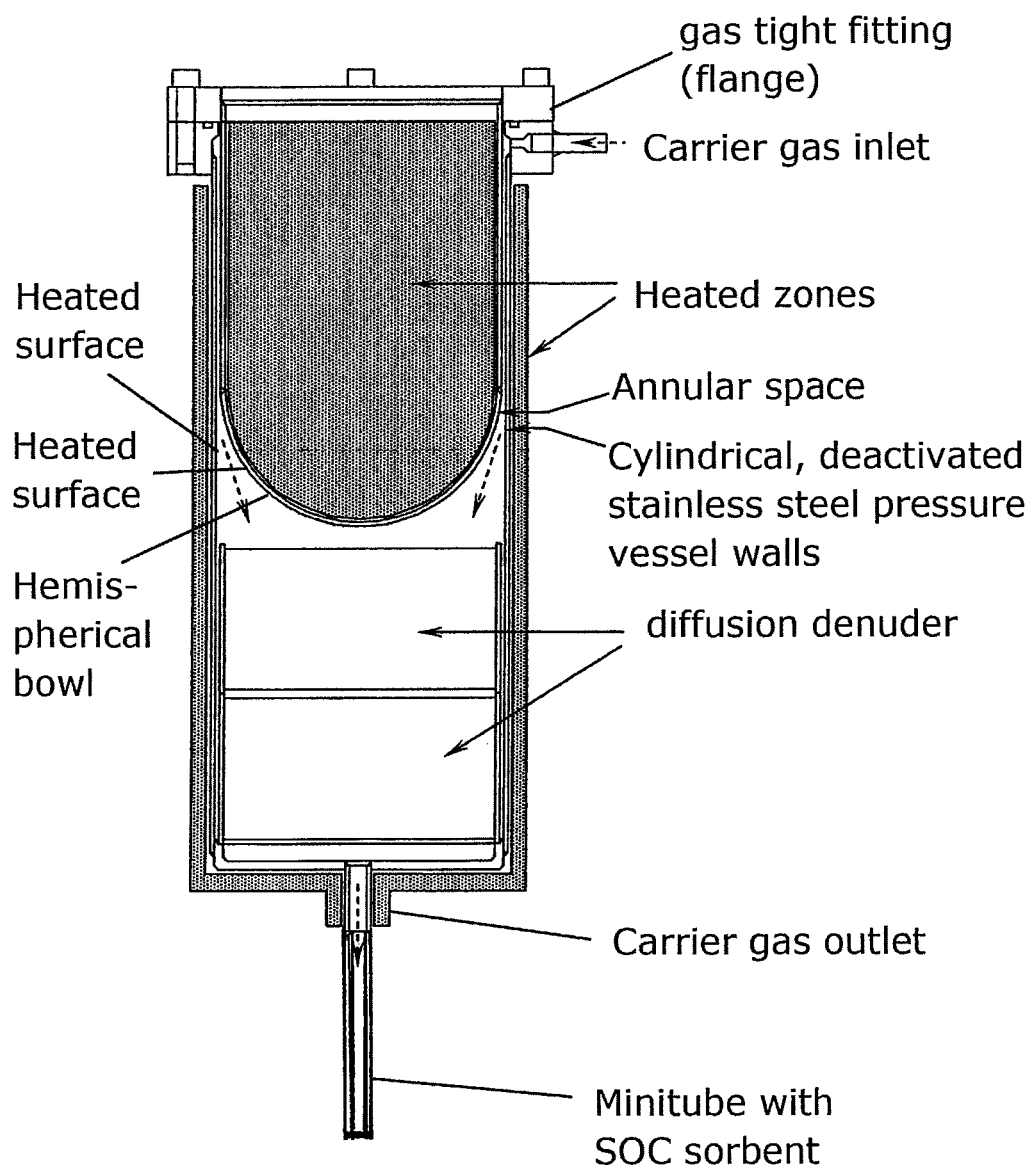
FIG. 3 depicts one embodiment of an analyte transfer apparatus.
Figure 4:
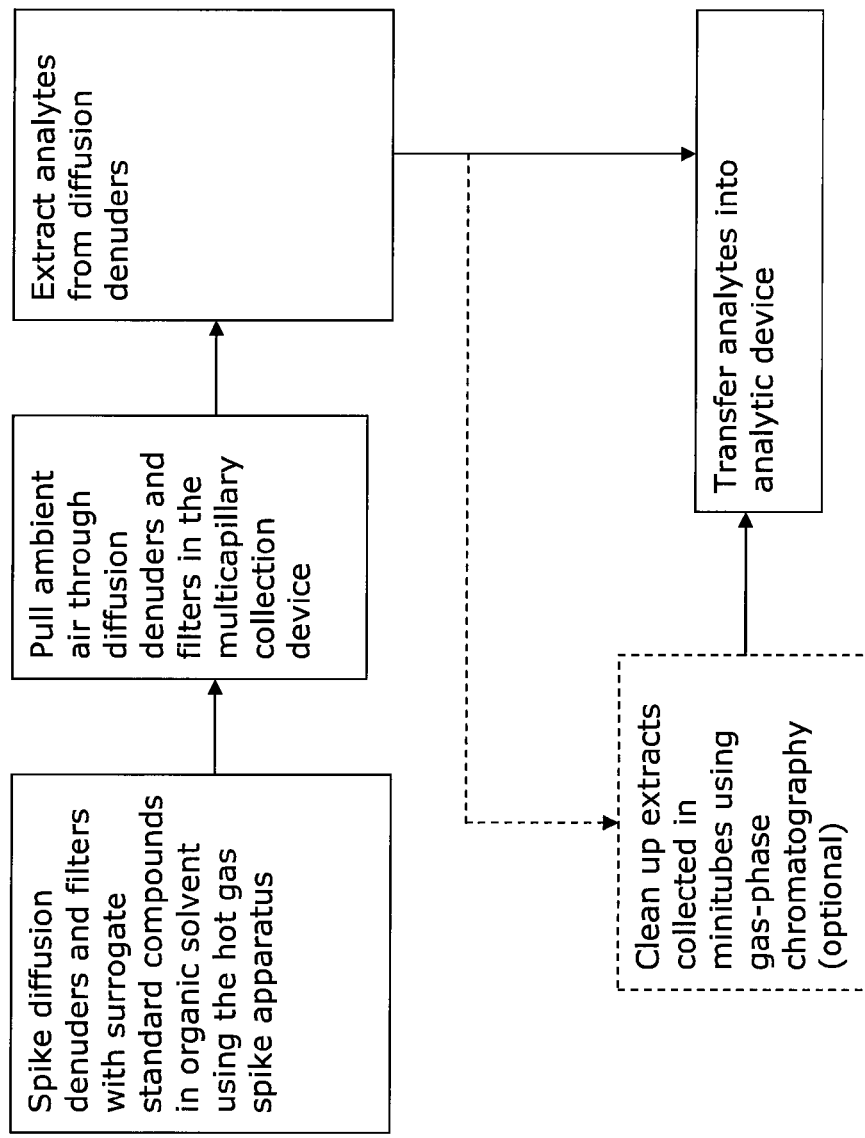
FIG. 4 is a process flowchart illustrating exemplary steps in semivolatile organic chemical collection from ambient air using multicapillary collection device, extraction and analysis.

The ATA (FIG. 3) can be used in the laboratory and in the field to transfer analytes from MCCDs into for example, such receptacles as minitubes, which can be stored, using gas-tight fittings, for later analysis. One embodiment of the apparatus includes a housing having temperature-controlled zones that are connected by a gas-tight fitting to a minitube. The first zone in the housing holds a diffusion denuder (described above) and is heated, for example, to 230 to 300° C. during the thermal extraction of analytes. Carrier gas (e.g., ultra-high purity helium or nitrogen; flow rate 1-5 L min$^{-1}$) enters the housing upstream of the diffusion denuder zone via an inlet with a gas-tight fitting.

The ATA transfer process provides the optional opportunity in the analyte transfer process for gas-phase sample cleanup. For example, in applications of analysis of specific SOCs in ambient air, water and polar organics present interfered with the SOCs without an additional cleanup step. The interfering water and polar organic compounds could be removed by inserting, for example, a minitube containing a polar sorbent between the ATA and the minitube containing SOC sorbent during ATA transfer to remove the polar interfering compounds from the gas stream prior to capture of SOCs in the minitube containing SOC sorbent.

Ambient temperature carrier gas flows through a narrow, annular space with heated surfaces on both sides. The zone serves several purposes:

1. Carrier gas is pre-heated while flowing through this zone prior to reaching the denuder, thus providing uniform heating to the center of the denuder;
2. The flange is extended outside of the heated zone, thus allowing for the use of an elastomer seal rather than graphite, metallic, or other high temperature seals that would be more costly, require more maintenance, and/or require higher sealing pressure; and
3. The flow of carrier gas through the narrow, annular section minimizes counter-current diffusion of analytes up through the annular section where they would condense on the cool flange, thus providing for quantitative transfer and preventing carryover of analytes surrogate standards from one run to the next.

A hemispherical bowl is optionally located inside the housing distributes the carrier gas flow evenly across the face of the diffusion denuder. A minitube is attached downstream of the diffusion denuder using a gas-tight fitting in a zone at ambient air temperature. In one embodiment, minitubes are made of stainless steel (Supelco, Inc.), deactivated (e.g., Sulfinert treatment, Restek) and packed with a sorbent media (e.g., chromosorb acid washed DMDCS deactivated material coated with 3% Rtx-1 stationary phase, 40/60 mesh, Restek). All heated metal surfaces of the ATA are deactivated (Sulfinert treatment, Restek). If chosen, ultra high purity helium carrier gas flows from 1-5 L min$^{-1}$ through the apparatus during transfer of analytes from the diffusion denuder into a minitube.

By elevating the temperature of the zone containing the diffusion denuder to about 230° C., target analytes are thermally extracted from the diffusion denuder and transferred in a carrier gas (such as nitrogen) into a cooler minitube, where the analytes are retained in sorbent media. Water collected in a MCCD can be removed during the transfer from the ATA into a minitube packed with hydrophobic Rtx-1 coated media. Water is not retained in such a minitube at 15° C., while target analytes are retained. This can be an advantage over prior work (e.g., Tobias et al. 2007, and others) where water caused analytical interferences or complex purging steps were required for water removal. A water purge prior to analyte transfer was avoided along with associated losses of more-volatile analytes.

Particle-associated SOCs collected on filters are analyzed after inserting a rolled filter into the same deactivated, blank stainless steel tubes used to custom-fabricate low flow diffusion denuders. In one approach, the analytes can be thermally extracted into a cryogenically-cooled programmable temperature-vaporization (PTV) inlet of a gas chromatograph in the same manner as gas-phase analytes trapped in sorbent media in the custom-fabricated minitubes following transfer using the ATA.

Thus, the invention includes a system to collect, concentrate, transfer and optionally clean up trace atmospheric SOCs to a gas chromatograph for analysis. Two objectives of the invention are to (1) obtain similar or better method detection limits for SOC measurement as compared to the conventional method using one-dimensional gas chromatography for polychlorinated biphenyl compounds, and (2) collect adequate analyte mass of gaseous and particle-associated analytes for quantification.

Also, in alternative embodiments and steps:
1. Sampling using MCCDs avoids artifacts in separation of particle and gas phase SOCs by using diffusion denuders upstream and downstream of a filter.
2. Reduced time required for sample collection by transferring virtually the entire mass of analyte in the sample to the gas chromatograph inlet.
3. The high sampling flow rates through MCCD required for SOCs present at $pg/m^3$ concentrations can be achieved at extremely low headloss and lower air retention time in the device.
4. Use of a re-usable sorbent cartridge, in the form of a denuder, does not require pre-cleaning or extraction with solvents or, likely, frequent regeneration.
5. Substantial savings can be realized in the time, expense, and solvent waste generation in the extraction and concentration process through use of thermal extraction in place of solvent extraction.

Other SOC sample collection and analysis systems that use diffusion denuders exist, but none have successfully used thermal extraction transfer into the gas chromatograph using a durable, re-usable denuder. Also, none have combined thermal extraction with sufficient sample capacity to offer method detection limits comparable to high-volume air sampling and analysis.

In comparison with prior approaches (each of the 3 being incorporated by reference):
1. Krieger & Hites (Krieger, M. S. and Hites, R. A. (1992). "Diffusion Denuder for the Collection of Semivolatille Organic Compounds". *Environ. Sci. Technol.* 26, 1551-1555.) used thermal extraction to directly transfer analytes collected in a diffusion denuder into a gas chromatograph. However, that denuder was not durable and did not stand up to repeated thermal extraction cycles. The inventive denuder is durable and re-usable in the thermal extraction process. It has approximately 10 times the sample capacity and 20 times the sampling flow rate (13 L min$^{-1}$ vs. 300 L min$^{-1}$) of the cited prior art denuder. The construction method used there—bundling gas chromatograph column lengths together—would not be practical for construction of a large-diameter, high flow rate denuder.
2. A primary advantage of the inventive denuder over that of Gundel et al. (Gundel, L. A. and Lane, D. A. (1999) "Sorbent-Coated Diffusion Denuders for Direct Measurement of Gas-partitioning by Semi-volatile Organic Compounds," *Gas and Particle Phase Measurements of Atmospheric Organic Compounds*. (Lane, D. A., Ed.) pp 287-332, Gordon and Breach Science Publishers, Amsterdam, The Netherlands.) is that it can be repeatedly re-used in the disclosed thermal extraction analyte transfer apparatus. The cited denuder must be solvent-extracted.
3. The denuder of Mader et al. (Mader, B. T., Flagan, R. C. and Seinfeld J. H. (2001) "Sampling atmospheric carbonaceous aerosols using a particle trap impactor/denuder sampler". Environ. Sci. technol., 35, 4857-4867, utilized a honeycomb element coated with activated carbon and operated at a flow rate of 300 L/min. Gaseous and particle-associated SOCs were solvent extracted from the denuder and filter respectively. Only particle-associated organic carbon concentration was reported.

Several features of the invention would not be obvious to those skilled in the art:
1. The system can transfer low-volatility, in some cases thermally labile compounds such as polybrominated diphenyl ethers, using thermal extraction, and in contact with large surface areas of stainless steel, and granular sorbent material, without substantial losses by degradation or irreversible sorption.
2. The system can collect analytes in mini-sorbent tubes at flow rates much higher than conventionally used (2 to 3 L/min vs. 40 mL/min).
3. The system includes an ATA that is capable of quantitative analyte transfer into minitubes in spite of the fact that the high-flow rate diffusion denuders must be desorbed at liters per minute, while the gas chromatograph column flow rate is on the order of 2 mL/min.
4. The ATA and HSGA provide for uniform gas flow and temperature control over a large diameter diffusion denuder.
5. The system can handle large volume samples that are solvent-free except for use in milliliter quantities as carrier solvent, and can employ an optional cleanup step capable of selectively removing interfering substances present in atmospheric samples while quantitatively transmitting SOC analytes.

Thus, one application of the invention is for measurement of gas and particle-associated SOC concentrations in indoor (e.g., a smokestack) and outdoor air. The transport, distribution, and environmental fate of some SOCs, including secondary organic aerosol precursors and persistent toxic substances, is of significant interest to researchers and policy makers because of their effects on climate and health of humans and wildlife. The invention has applications in any situation in which it is necessary to measure trace concentrations of organic compounds in air. The invention can be used with micrometeorological instrumentation for measuring air/surface exchange fluxes of SOCs over land or water.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An atmosphere sampling and extraction system, comprising:
    a collection device comprising
        a housing;
        at least one diffusion denuder contained in the housing, the diffusion denuder having a plurality of capillaries coated with a stationary phase for capturing gaseous semivolatile organic compounds (SOCs);
    a hot gas spike apparatus connectable to the diffusion denuder for introducing a compound into the diffusion denuder; and
    an analyte transfer apparatus connectable to the diffusion denuder for extracting the SOCs from the at least one diffusion denuder.

2. The atmosphere sampling and extraction system of claim 1 wherein the collection device further comprises:
    a filter support connected to the housing downstream of the at least one diffusion denuder; and a filter positioned in the filter housing for collecting the particles and the particle-associated SOCs from the atmosphere.

3. The atmosphere sampling and extraction system of claim 2 comprising at least one additional diffusion denuder that is positioned downstream of the filter support.

4. The atmosphere sampling and extraction system of claim 1 wherein the at least one diffusion denuder permits a flow rate of approximately 600 L min$^{-1}$.

5. The atmosphere sampling and extraction system of claim 1 wherein the compound provided to the at least one diffusion denuder by the hot gas spike apparatus is at least one of the group consisting of a target analyte, an internal standard, and a surrogate standard.

6. The atmosphere sampling and extraction system of claim 1 wherein the plurality of capillaries of the diffusion denuder are contained within a thermally stable encapsulating medium.

7. The atmosphere sampling and extraction system of claim 1 wherein the stationary phase is a crosslinked polydimethylsiloxane.

8. The atmosphere sampling and extraction system of claim 1 wherein the plurality of capillaries of the at least one diffusion denuder are fabricated from a ceramic.

9. The atmosphere sampling and extraction system of claim 1 wherein the plurality of capillaries of the at least one diffusion denuder are fabricated from fused silica and contained within a thermally stable encapsulating medium.

10. The atmosphere sampling and extraction system of claim 1 wherein the plurality of capillaries of the at least one diffusion denuder are fabricated from stainless steel.

11. The atmosphere sampling and extraction system of claim 1 wherein the hot gas spike apparatus comprises a cylindrical mixing chamber having a carrier gas inlet and a makeup gas inlet, wherein the carrier gas inlet is perpendicular to the makeup gas inlet, and the carrier gas inlet is tangential to a wall of the cylindrical mixing chamber.

12. The atmosphere sampling and extraction system of claim 1 wherein the analyte transfer apparatus comprises a vessel for containing the at least one diffusion denuder, the vessel having a temperature-controlled zone able to heat the at least one diffusion denuder therein to a temperature in a range of at least about 230° C. to about 300° C. during extraction of analytes therein.

13. The atmosphere sampling and extraction system of claim 12 wherein the analyte transfer apparatus comprises a heated cylinder in a position upstream of where the at least one diffusion denuder is positioned in the vessel, wherein a narrow annular space is present between the vessel and the heated cylinder, wherein is created a heated annular zone that pre-heats a carrier gas while the carrier gas flows therethrough prior to reaching the at least one diffusion denuder, thus providing uniform heating of the carrier gas to a central region of the at least one diffusion denuder, the flow of carrier gas through the annular zone preventing diffusion of analytes up through the heated annular zone to avoid condensation of analytes thereon, the analyte transfer apparatus having a flange that extends outside of the heated annular zone.

14. The atmosphere sampling and extraction system of claim 13 wherein the heated cylinder further comprises a hemispherical bowl connected to a lower end thereof for distributing the carrier gas evenly across a face of the at least one diffusion denuder.

15. The atmosphere sampling and extraction system of claim 12 wherein the vessel of the analyte transfer apparatus comprises an outlet connectable to a minitube for retaining SOCs extracted from the at least one diffusion denuder.

16. The atmosphere sampling and extraction system of claim 15 wherein the minitube contains an SOC sorbent medium that is able to selectively retain the extracted SOCs but that does not retain water and/or other polar interfering compounds.

17. The atmosphere sampling and extraction system of claim 16 further comprising an intermediate minitube upstream of the SOC sorbent minitube that contains a polar sorbent medium able to retain water and/or other polar interfering compounds while allowing the extracted SOCs to be transferred into the minitube containing the SOC absorbent medium.

18. The atmosphere sampling and extraction system of claim 15 wherein the vessel of the analyte transfer apparatus comprises an outlet connectable to an analytic device for receiving SOCs extracted from the diffusion denuder.

* * * * *